United States Patent

Timms

[11] Patent Number: 5,819,747
[45] Date of Patent: Oct. 13, 1998

[54] IMMOBILIZATION VEST

[76] Inventor: M. Rick Timms, 1 Noble Glen Dr., Savannah, Ga. 31406

[21] Appl. No.: 775,923

[22] Filed: Jan. 2, 1997

[51] Int. Cl.$^6$ ..................................................... A61B 19/00
[52] U.S. Cl. ........................... 128/869; 128/870; 128/874
[58] Field of Search .................................... 128/845, 846, 128/869, 870, 876; 5/630, 636, 638, 640

[56] References Cited

U.S. PATENT DOCUMENTS

| | | | |
|---|---|---|---|
| 1,696,559 | 12/1928 | Ward | 128/875 |
| 1,916,789 | 7/1933 | Fordham . | |
| 3,315,671 | 4/1967 | Creelman | 128/870 |
| 3,641,997 | 2/1972 | Posey | 128/874 |
| 4,024,861 | 5/1977 | Vincent . | |
| 4,034,748 | 7/1977 | Winner | 128/870 |
| 4,151,842 | 5/1979 | Miller . | |
| 4,211,218 | 7/1980 | Kendrick . | |
| 4,589,407 | 5/1986 | Koledin et al. . | |
| 4,593,788 | 6/1986 | Miller . | |
| 4,594,999 | 6/1986 | Nesbitt . | |
| 4,665,908 | 5/1987 | Calkin | 128/870 |

*Primary Examiner*—Michael A. Brown
*Attorney, Agent, or Firm*—McAndrews, Held & Malloy, Ltd.

[57] ABSTRACT

A spinal immobilizer extrication vest designed to be compact and easily applied to accident victims in confined spaces, such as deformed structures of automobiles, or applied following structure collapse. The device is constructed of lightweight nylon material, with rigid longitudinal cylindrical rods which, in addition to intrinsic rigidity form a stiffening arc when the rods are applied about the victim and secured anteriorly, by two overlapping nylon body panels with hook fastener and loop fastener material. Contiguous ear panels augment head immobilization, provided by prior application of a rigid cervical collar. Following placement of such a collar, the vest is positioned, body panels are opened beneath the victim's arms and wrapped around the victim providing cervical, thoracic and lumbar immobilization. Sacral and pelvic support is provided by a triangular cradle of nylon material which extends from the lower edge of the central body panel. The pelvic cradle is positioned under the sacrum by passage behind either leg of a single strap, extending from the apex of the triangular cradle. Pulling the strap inferiorly advances the pelvic cradle under the sacrum and buttocks. The strap is then pulled superiorly through the crotch to fasten anteriorly by hook fastener and loop fastener material to the outside of the secured, overlapping body panels. Seven lifting straps are located to facilitate controlled movement of the immobilized victim.

26 Claims, 3 Drawing Sheets

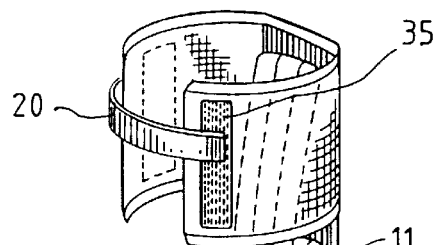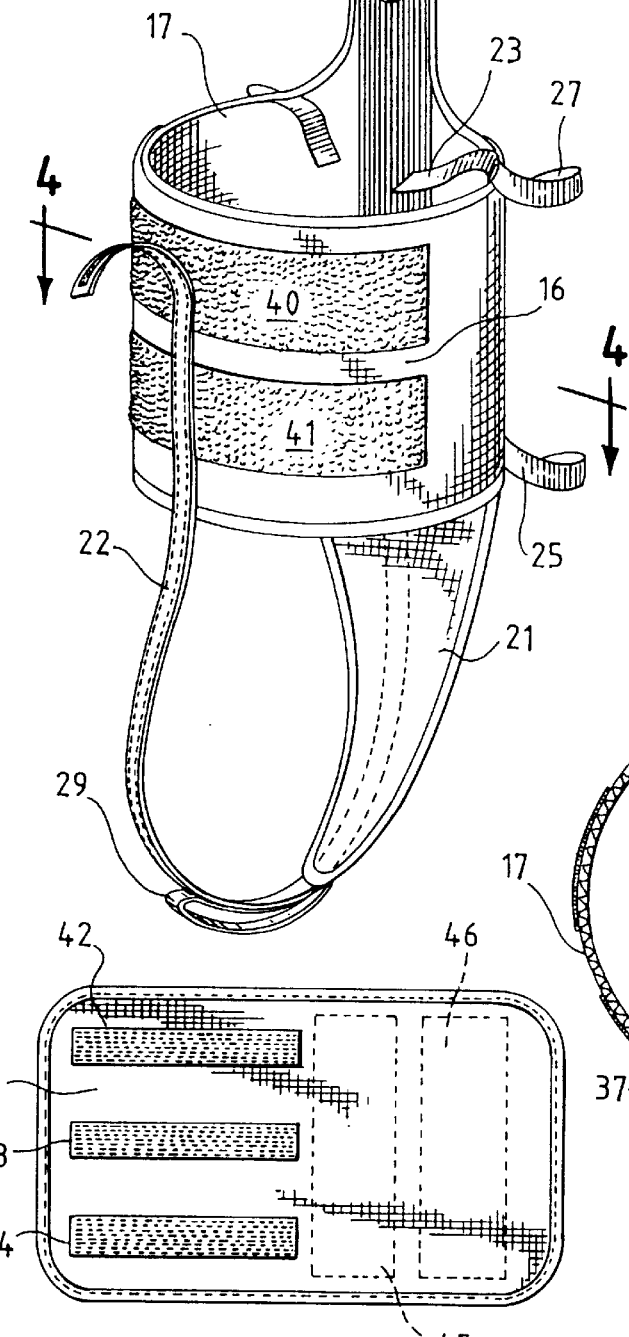

IMMOBILIZATION VEST

BACKGROUND OF THE INVENTION

1. Field of the Invention

The present invention relates to rescue apparatus and spinal immobilizers designed to facilitate safe removal of injured persons from confined spaces, such as passenger compartments of deformed automobiles, or collapsed buildings.

2. Description of the Prior Art

Accident victims are subject to injury of the spine and require immobilization at the accident site to permit transport to medical facilities for evaluation. Such immobilization may be provided by a variety of devices, including a simple board with tie downs, straps and buckles, combined with padding and strapping of the head to the rigid backboard. Such full length devices are useful in open areas, but cannot be placed under or behind injured persons in confined spaces. Several devices serving as short spine immobilizers exist utilizing a variety of materials, ranging from plasticized nylon to cardboard, and each incorporates a rigid panel or series of slats or a rigid material which is contained in pockets within the device or may be inserted after application of the device onto the injured person. Many configurations of straps and buckle arrangements contribute to the prior art.

Due to the requirement for functional rigidity, most examples of prior art utilize flat slats of woods, metal or plastic materials encased in a plasticized or nylon material, and feature closure systems involving straps and buckle systems of varying complexity. These are generally difficult and time consuming to apply, particularly when application is attempted by a single rescuer. Although considered short spine immobilizers, examples of the existing prior art are often difficult to use in small or confined spaces, re-package following use, and store within the rescue vehicles. The size and complexity of such devices has limited their use in situations requiring lightweight, compact, portability into remote or isolated areas, i.e., mountain rescue or military application.

SUMMARY OF THE INVENTION

A spinal immobilizer or immobilization vest is designed to be compact and easily applied to accident victims in confined spaces, such as deformed structures of automobiles or following structure collapse The device is constructed of lightweight nylon material, with longitudinal rigidity provided by a plurality of cylindrical stiffening rods which when applied to the victim, provide additional longitudinal rigidity related to the tubular rigidity provided by the formation of an arc of the individual stiffening elements. The rods provide some rotational flexibility to the vest prior to positioning, thus permitting placement and application of the vest in a confined space. The vest, which in the preferred embodiment measures three inches (3)" in diameter by 30" in length, may be placed behind a victim, and secured by two nylon full wrap body panels which utilize large surfaces of mateable hook fastener and loop fastener material to close the device anteriorly around the thorax and abdomen. Preferably, the head and neck are first stabilized by a conventional cervical collar (not part of the vest) and then ear flaps of the vest which utilize hook fastener and loop fastener material further immobilize the head and neck and secures the head to the upper portion of the central panel of the vest. The lower body is secured by a triangular flap with a single strap extension, featuring hook fastener and loop fastener material which, after passing under or behind the victim's knees, is used to position the triangular flap of nylon material which provides a cradle of support for the sacrum and pelvis. The combination of compact size, and rotational flexibility provided by use of rigid tubular stiffeners permits placement of the device in confined spaces. Spinal immobilization is ensured by the intrinsic rigidity of the cylindrical stiffeners, which is augmented by the additional longitudinal rigidity of the tubular arc formed by the stiffeners when applied to an injured person.

The use of a triangular panel to provide for pelvic and sacral support in a cradle of nylon material which is easily positioned by a single strap requiring no buckles or fasteners is particularly advantageous. Once positioned, the device facilitates lifting and removal of the victim from the space by rescuers, utilizing seven lifting straps oriented to provide for ease of lifting and to assist in maintaining proper positioning of the device on the patient. As is the case with all short spinal immobilizers, this device is intended to be used in conjunction with a separate head cervical collar device, and subsequent immobilization of the injured person on a long spine board system for transport to a definitive care facility. The ease of use, speed of application, and immobilization provided by use of round stiffeners, full wrap body panels and a pelvic cradle distinguish this device from prior art.

These and other advantages are discussed in the following description.

BRIEF DESCRIPTION OF THE DRAWINGS

FIG. 3 is a perspective view of the vest of FIG. 1 in the configuration as applied to a person.

FIG. 4 is a cross-section of the vest of FIG. 1 at the level of the body panels along line 1—1 in FIG. 3.

FIG. 5 is a top perspective of a body panel extender for use with the vest of FIG. 1.

DESCRIPTION OF THE PREFERRED EMBODIMENT

Figure 1:
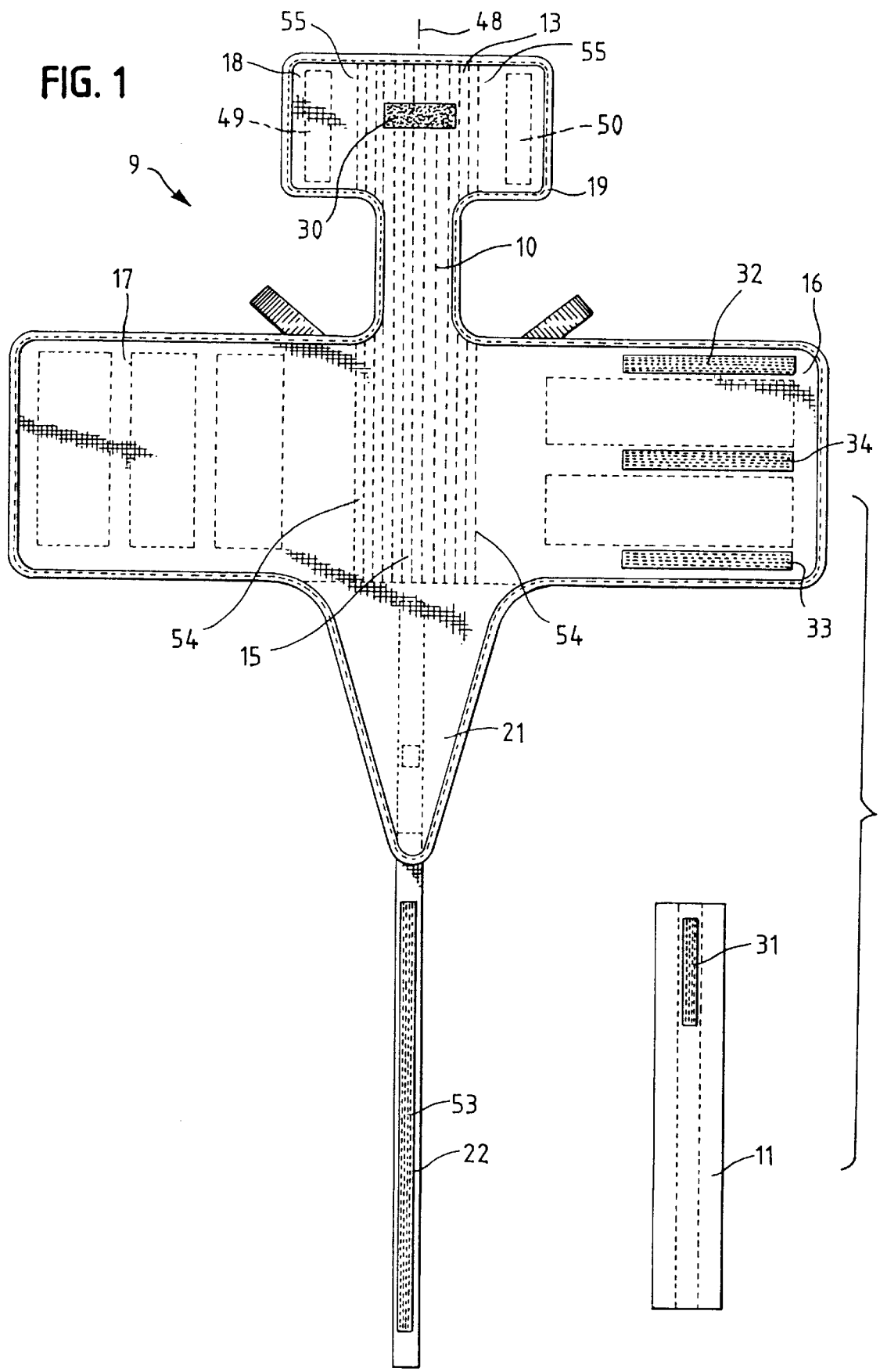
FIG. 1 is a top perspective of an embodiment of an immobilization vest.

An immobilization vest 9, was developed to provide a rapid immobilization of the spine of an accident victim by a single rescuer in a confined space. Vest 9 utilizes several features to facilitate ease of application, cleaning and storage. Referring to FIG. 1, vest 9 comprises an immobilizer portion 10, a separate head strap 20 and a separate head pad/neck roll portion 11. In addition, a body panel extender 12 (FIG. 5) may be used with the vest, as described hereinafter.

The vest is constructed as a lightweight, thin appliance, formed from two layers of a coated, ripstop nylon fabric. The fabric layers are sewn together in a manner to establish multiple longitudinal pockets 13 which locate a series of longitudinal stiffeners 14 (FIG. 4). Each stiffener 14 is a ⅜ inch diameter cylindrical rod formed of either wood, aluminum, or fiber material. For example, a solid Birch wood dowel may be used, or an aluminum tube, etc. The longitudinal rigidity required is provided by approximately six (6) stiffening rods 14 located side-by-side along the longitudinal axis 48 of the device. Rods 14 extends from the top to the bottom of a central body panel 15. Panel 15 is approximately 5" wide and 30" long.

Contiguous with and extending laterally from each side of panel 15 are side body panels 16, 17. Panels 16, 17 are formed from the same double layers of nylon fabric forming central panel 15. Each panel 16, 17 carries mateable hook fastener material and loop fastener material (for example Velcro® brand materials) arranged on the vest at locations to provide closure or securement of the panels 16, 17 around the anterior, ventral surface of the injured person. The full width of vest 9 measures approximately 48" from the outer edges of the two body panels 16, 17. Each panel 16, 17 measures 14" in the direction of the longitudinal axis 48 and 21-½" in the direction orthogonal to axis 48.

Two cushioned ear flaps 18, 19 extend laterally from central panel 15 at the location where the head of the injured person will rest. Each ear flap is approximately 8" in height. A piece of material (fabric, meshed webbing, etc., not shown) may be sewn between the two fabric layers making up the ear panels 18, 19 in order to provide cushioning, at 49, 50.

Each ear flap 18, 19 is secured against the head of the injured person using a 24"×2" nylon webbing strap 20 (FIG. 3). A 1.5" loop fastener material is sewn on the strap 20 in order to engage with hook fastener material 35, 36 (FIG. 2) sewn to the posterior side of each flap 18, 19. Flaps 18, 19 are designed to augment head immobilization which is provided by the prior application to the injured person of a conventional rigid cervical collar (not shown).

A triangular "diaper" flap 21 and a single strap 22 of 1.5" high visibility nylon webbing is used to secure the lower body of the injured person. A ¾" hook fastener material is attached to strap 22 which extends from the apex of the triangular flap 21. The base of the triangular flap is contiguous with the lower edge of central panel 15 and measures 14" across at the triangle's base. The triangular flap extends 16" along the longitudinal axis (the triangle's height) The pelvic strap 22 extends from the mid portion of the triangle's base, through the apex of the triangular flap and continuing for an additional 32" along the longitudinal axis for a total length of 48" forming a cradle and strap. Strap 22 is passed behind the victim's knee and then is pulled inferiorly to pull the pelvic cradle into position beneath the sacrum and pelvic. Once the triangular flap 21 of nylon material is positioned so as to provide support for the sacrum and pelvis, strap 22 is secured to exposed fastener loops on the outer body panel 16, described hereinafter. Strap 22, as well as other portions of the device, may be colored bright orange, for example.

The entire vest, including central panel 15, body panels 16, 17, ear flaps 18, 19 and the pelvic triangular flap 21 is constructed of a single, continuous 48" wide sheet of coated nylon fabric which is folded into a double layer. The coating may be a waterproof coating on one side of the fabric which is the side folded back on itself. The pattern shown in FIG. 1 is cut and sewn together utilizing a nylon thread. The longitudinal pockets 13 are sewn, a ½" nylon binding is sewn around the outer edge. Also, sections of hook fastener and loop fastener material are sewn into position.

Figure 2:
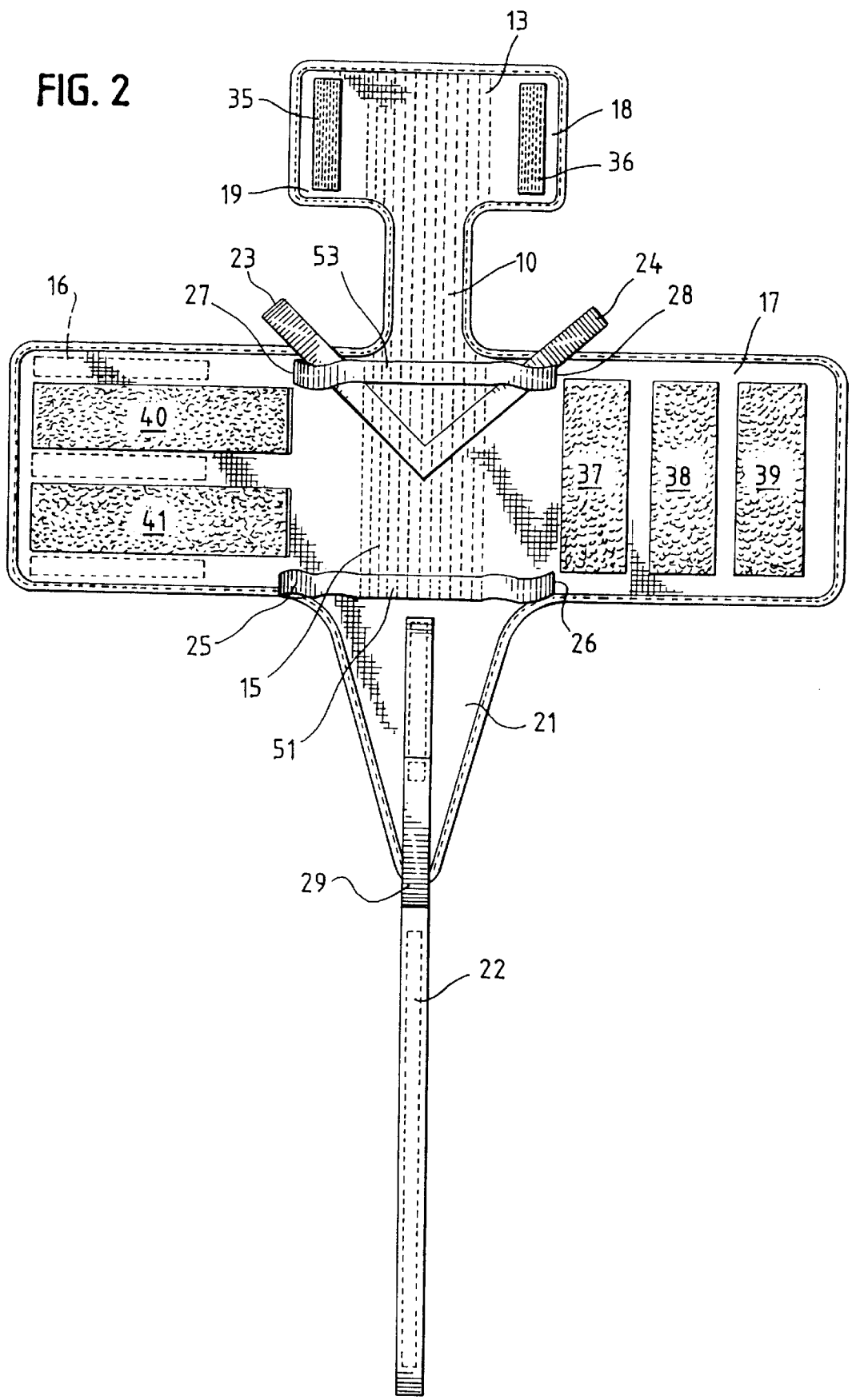
FIG. 2 is a bottom perspective of the vest of FIG. 1.

Also sewn into position as seen in FIG. 2, are seven 1.5" nylon webbing straps 23, 24, 25, 26, 27, 28, and 29, which provide for lifting the injured person with the vest properly applied to the person. Each of the lifting straps are folded double and sewn to the vest to produce a loop which measures 5" when flattened, i.e., approximately a 10" loop. Lifting straps 23, 24 are located at the junction of the central panel 15 and the top of the two body panels 16, 17. The lifting straps 23, 24 are oriented at a 45 degree angle to the longitudinal stiffeners. Straps 23, 24 extend beyond the point of sewn attachment, extending medially and inferiorly to meet at the midline of the central panel, approximately 7" above the bottom of the central panel, as shown in FIG. 2. The extension of straps 23, 24 may be sewn secure as well, incorporated into the stitching for pockets 13.

Also sewn transversely to the posterior surface of the vest, and incorporated into the stitching for the longitudinal pockets 13, are two 1.5" webbing straps 51, 53 located at the base of the central panel and across the central panel and located at the level of the top of the body panels 16, 17 as shown in FIG. 2. The ends of these two straps are formed into the transverse lifting straps 25, 26, 27, 28, as shown. Lifting strap 29 is located at the apex of the triangular flap 21, and is sewn onto the posterior surface of the pelvic strap 22. When applied to an injured person, lifting strap 29 is oriented superiorly at the level of the anterior supra pubic area and assists in maintaining proper positioning of the device on the injured person, specifically limiting the cephalad migration of the device.

The device utilizes mateable hook fastener and loop fastener material in a manner specifically designed to facilitate closure of the body panels 16, 17 and attachment of the head pad 11, head strap 20, body panel extender 12 (FIG. 5), and pelvic cradle strap 22. As seen in FIG. 1, the anterior surface of the device has, attached by sewing with nylon thread, a 5" section of 1" wide loop fastener material 30 which is oriented transversely to axis 48, at a point 3" below the top of the vest, for attachment of the head pad 11. A 5" section of 1" hook fastener material 31 is sewn to the upper portion of the head pad 11, and oriented longitudinally, as shown, to permit optimum positioning of the head pad.

Also on the anterior surface of the device, three 16" sections of 1" hook material 32, 33, 34 are sewn to body panel 16 in a transverse orientation to axis 48 at positions 1" from the top and bottom of the panel and a third at the mid portion of the panel. Also attached to the pelvic cradle strap 22 by sewing is a 28" long section of ¾" hoop fastener material 53, which facilitates attachment of the pelvic strap 22 to the loop fastener material on the posterior surface of body panel 16.

In FIG. 2 is shown the location of the hook fastener and loop fastener material sewn to the posterior surface of the device. Strips 35, 36 of 1.5" wide hook fastener material, measuring 6.5" in length, are oriented longitudinally in a position 1" from the end of the two ear flaps 18, 19. These serve as attachments to the loop fastener material sewn to the nylon webbing head strap 20 (FIG. 3).

Referring again to FIG. 2, the posterior surface of body panel 17, is occupied by three sections of loop fastener material 37, 38, 39, each measuring 4" by 11", and sewn in longitudinal orientation to axis 48. Body panel 16, has two sections of loop fastener material 40, 41 oriented transversely to axis 48, each measuring 4" by 16" and located 2" from the top and bottom of the panel 16, and extending to a point 2.5" from the outer edge of the body panel 16.

FIG. 3 shows the device in its wrapped configuration as applied to an injured person, with FIG. 4 providing a cross-sectional view from the base of the device observing cephalad, at the level of Line 1—1 in FIG. 3. The head strap 20 is attached to ear flaps 18, 19, and body panel 16 overlaps body panel 17 with attachment by hook fastener material 32 and loop fastener material 38. The head pad/neck roll 11 is shown in its rolled up position, and pelvic strap extension 22 is attached to the loop fastener material 40, 41 on the surface of body panel 16.

The device may be stored in a variety of configurations, but preferentially with the triangular pelvic cradle flap 21 and strap 22 folded anteriorly to lie adjacent to the anterior surface of the central body panel 15 containing the stiffening rods. The head strap 20 is attached by matched hook fastener and loop fastener material to the pelvic strap 22 for storage. The side body panels 16, 17 are folded to properly orient the hook fastener and loop fastener material, and then rolled into a 3" diameter roll which measures 30" in length.

Referring to FIG. 5, a separate body panel extender 12 measures 24" in width by 14" in height. Hook fastener material 42, 43, 44 is sewn on one surface of extender 12 and loop fastener material 45, 46 is sewn on the other surface. The fastener materials 42–46 are oriented to attach to the body panels 16, 17 of the vest, which permits application of the extended vest to a large adult injured person. Extender panel 12, as shown in FIG. 5, also serves to wrap the device in its rolled configuration for storage in a supplied nylon bag (not shown) with flap top closure and carrying strap. A 24" by 5" head pad 11 is provided which attaches via hook fastener and loop fastener material to the head section of the device. The lower portion of this pad can be rolled superiorly to provide a suitable neck roll of the desired thickness.

This vest provides for the rapid application of a short spinal immobilizer, in confined spaces due to the compact size of the device, and the use of integral body panels and hook and loop fasteners. The longitudinal rigidity is provided by six (6) cylindrical ⅜" stiffeners 14, each 30" in length, located in longitudinal pockets 13 in the central panel created by sewing together of the dual layers of nylon material.

In the preferred embodiment, three additional ⅜" diameter cylindrical stiffeners 54 of 13"–15" in length are located at the medial aspect of each body panel 16, 17 adjacent to the central panel. Three additional ⅜" diameter cylindrical 55 stiffeners measuring 6" in length are also incorporated into the medial portion of each ear flap 18, 19. Although the six (6) full length rods 14 and twelve (12) short rigid rods 54, 56 offer intrinsic longitudinal rigidity to the vest, there is sufficient rotational flexibility of the vest to permit placement in small confined spaces. The application of the vest, with formation of a posterior arc of cylindrical stiffening rods and the anterior re-enforcement of the abdominal wall and thoracic cage by the full wrap body panels, provides additional rigidity associated with formation of a tubular structure.

In operation, the vest may be placed behind a seated person while rolled, with extension and closure of the body panels 16, 17, the ear flaps 18, 19 and the triangular pelvic cradle 21. Alternatively, the vest can be opened, unrolled and positioned behind an upright, seated or recumbent victim as required by the rescuer. The body panels are secured by overlapping the left body panel 16 onto the right body panel 17, securing the ear flaps 18, 19 with the head strap 20, and passing the pelvic strap 22 under either knee to position the pelvic cradle 21. Once secure, the patient may be lifted safely by multiple rescuers utilizing the seven lifting straps 23–29 provided.

The vest has particular usefulness in applications such as immobilization and removal of race drivers from extremely confining cockpits of single seat race cars. Further, the vest may also be utilized as an extremity immobilizer by placing the ear flaps 18, 19 at the level of the ankle or wrist, while the body panels 16, 17 are secured at the level of the thigh or upper arm. Additionally, the vest serves as a total body wrap, pediatric immobilizer for small children and large infants.

What is claimed is:

1. An immobilization vest for use to stabilize an injured person, said immobilization vest comprising:
   (a) a central panel having a longitudinal axis;
   (b) at least two side panels transverse to said longitudinal axis;
   (c) at least one ear flap transverse to said longitudinal axis; and
   (d) a pelvic support panel connected to said central panel, said pelvic support panel comprising:
      (d)(1) a flexible flap shaped and positioned on said central panel to be pulled into position between the legs of said injured person to provide support for the sacrum and pelvis of said injured person: and
      (d)(2) a securing strap attached to said flexible flap, said securing strap positioned on said flexible flap to pull said flexible flap into position between the legs of said injured person.

2. The immobilization vest of claim 1, further comprising at least one body panel extender attached to one of said at least two side panels, said body panel extender thereby forming a continuation of said at least one side panel and extending the circumference around which said immobilization vest may wrap.

3. The immobilization vest of claim 1, wherein a flexible hook fastener is attached to at least one of said at least two side panels.

4. The immobilization vest of claim 3, wherein a flexible loop fastener is attached to at least one of said at least two side panels.

5. The immobilization vest of claim 1, further comprising at least one stiffening rod disposed in parallel alignment to said longitudinal axis and located inside at least one of said at least two side panels.

6. The immobilization vest of claim 1, further comprising a plurality of lifting straps attached to said immobilization vest.

7. The immobilization vest of claim 1, further comprising at least one cylindrical stiffening rod disposed in parallel alignment to said longitudinal axis and located inside said central panel, said at least one cylindrical stiffening rod providing additional longitudinal rigidity for said central panel, and wherein said at least two side panels close around an anterior ventral surface of said injured person to form a tubular wrap with said central panel forming a rigid arc posteriorly about said injured person when said at least two side panels are closed.

8. The immobilization device of claim 1, wherein said flexible flap is a triangular flexible flap and wherein said securing strap is attached to an apex of said triangular flexible flap.

9. The immobilization device of claim 1, further comprising at least one stiffening rod disposed in parallel alignment to said longitudinal axis and located inside said at least one ear flap.

10. An immobilization vest for use to stabilize an injured person, said immobilization vest comprising:
   a shaped light weight flexible wrapping comprising:
      (a) a central panel having a longitudinal axis;
      (b) at least two side panels transverse to said longitudinal axis;
      (c) at least one ear flap transverse to said longitudinal axis; and
      (d) a pelvic support panel connected to said central panel, said pelvic support panel comprising:
         (d)(1) a flexible flap shaped and positioned on said central panel to be pulled into position between the legs of said injured person to provide support for the sacrum and pelvis of said injured person: and (d)(2) a securing strap attached to said flexible flap, said securing strap positioned on said flexible flap to pull said flexible flap into position between the legs of said injured person: and a plurality of stiffening rods disposed in parallel alignment to said longitudinal axis and located inside said central panel.

11. The immobilization vest of claim 10, further comprising at least one body panel extender attached to one of said at least two side panels, said body panel extender thereby forming a continuation of said at least one side panel and extending the circumference around which said immobilization vest may wrap.

12. The immobilization vest of claim 10, wherein a flexible hook fastener is attached to at least one of said at least two side panels.

13. The immobilization vest of claim 12, wherein a flexible loop fastener is attached to at least one of said at least two side panels.

14. The immobilization vest of claim 10, further comprising at least one stiffening rod disposed in parallel alignment to said longitudinal axis and located inside at least one of said at least two side panels.

15. The immobilization vest of claim 10, further comprising a plurality of lifting straps attached to said immobilization vest.

16. The immobilization vest of claim 10, wherein said plurality of stiffening rods are cylindrical and provide additional longitudinal rigidity for said central panel, and wherein said at least two side panels close around an anterior ventral surface of said injured person to form a tubular wrap with said central panel forming a rigid arc posteriorly about said injured person when said at least two side panels are closed.

17. The immobilization device of claim 10, wherein said flexible flap is a triangular flexible flap and wherein said securing strap is attached to an apex of said triangular flexible flap.

18. The immobilization device of claim 10, further comprising at least one stiffening rod disposed in parallel alignment to said longitudinal axis and located inside said at least one ear flap.

19. An immobilization vest for use to stabilize an injured person, said immobilization vest comprising:

a shaped light weight flexible wrapping comprising:
(a) a central panel having a longitudinal axis;
(b) at least two side panels transverse to said longitudinal axis;
(c) at least one ear flap transverse to said longitudinal axis; and
(d) a pelvic support panel connected to said central panel, said pelvic support panel comprising:
(d)(1) a flexible flap shaped and positioned on said central panel to be pulled into position between the legs of said injured person to provide support for the sacrum and pelvis of said injured person: and
(d)(2) a securing strap attached to said flexible flap, said securing strap positioned on said flexible flap to pull said flexible flap into position between the legs of said injured person: and a plurality of stiffening rods disposed in parallel alignment to said longitudinal axis and located inside said central panel;

said at least two side panels closing around an anterior ventral surface of said injured person to form a tubular wrap with said central panel forming a rigid arc posteriorly about said injured person when said at least two side panels are closed.

20. The immobilization vest of claim 14, wherein a flexible hook fastener is attached to at least one of said at least two side panels.

21. The immobilization vest of claim 20, wherein a flexible loop fastener is attached to at least one of said at least two side panels.

22. The immobilization vest of claim 19, further comprising at least one stiffening rod disposed in parallel alignment to said longitudinal axis and located inside at least one of said at least two side panels.

23. The immobilization vest of claim 19, further comprising a plurality of lifting straps attached to said immobilization vest.

24. The immobilization vest of claim 23, wherein said lifting straps are attached at junctions between said central panel and said at least two side panels to direct applied lifting forces along said longitudinal axis.

25. The immobilization device of claim 19, wherein said flexible flap is a triangular flexible flap and wherein said securing strap is attached to an apex of said triangular flexible flap.

26. The immobilization device of claim 19, further comprising at least one stiffening rod disposed in parallel alignment to said longitudinal axis and located inside said at least one ear flap.

* * * * *